United States Patent [19]

Valen

[11] Patent Number: 5,007,835

[45] Date of Patent: Apr. 16, 1991

[54] DENTAL IMPLANT

[76] Inventor: Maurice Valen, 198-45 Foothill Ave., Holliswood, N.Y. 11423

[21] Appl. No.: 394,906

[22] Filed: Aug. 17, 1989

[51] Int. Cl.$^5$ .............................................. A61C 8/00
[52] U.S. Cl. .................................................. 433/174
[58] Field of Search ................. 433/173, 174, 175, 225

[56] References Cited

U.S. PATENT DOCUMENTS

| | | | |
|---|---|---|---|
| 3,435,526 | 4/1969 | Brancato | 433/174 |
| 3,590,485 | 7/1969 | Chercheve | 433/174 |
| 4,668,191 | 5/1987 | Plischka | 433/174 |
| 4,832,601 | 5/1989 | Linden | 433/173 |

FOREIGN PATENT DOCUMENTS 2184357  6/1987  United Kingdom ................ 433/173

Primary Examiner—Cary E. Stone
Attorney, Agent, or Firm—Salzman & Levy

[57] ABSTRACT

A screw-typed dental implant is featured having rounded threads for providing a controlled radial osteocompressive force against the threaded wall of bone tissue that was previously drilled and tapped. The thread profile provided by the tap is undercut below the external thread surface of the implant causing a compressive force to be exerted against the bone wall. The taps are designed to provide a given thread surface by varying the pitch angle. In this fashion, a greater undercut is provided for mandibular bone tissue as compared to maxillary bone tissue.

20 Claims, 2 Drawing Sheets

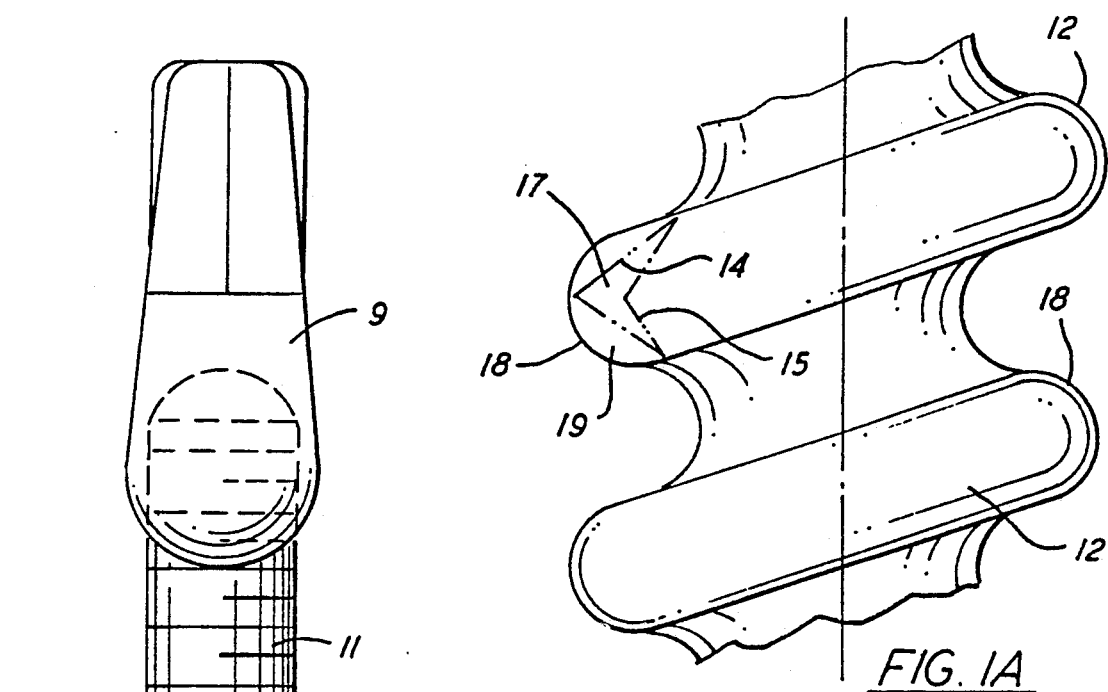
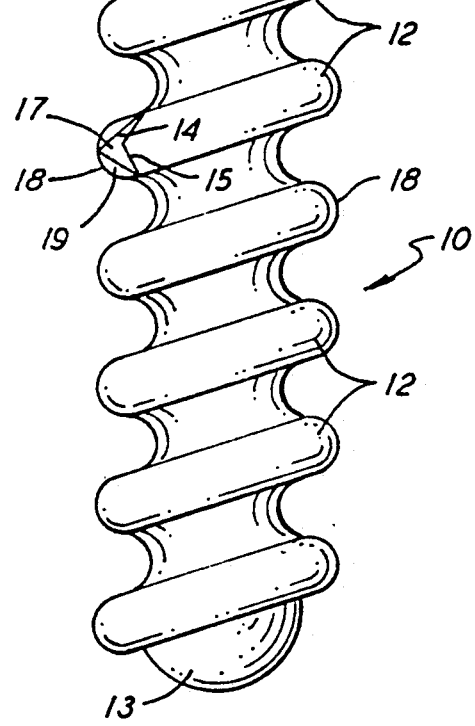
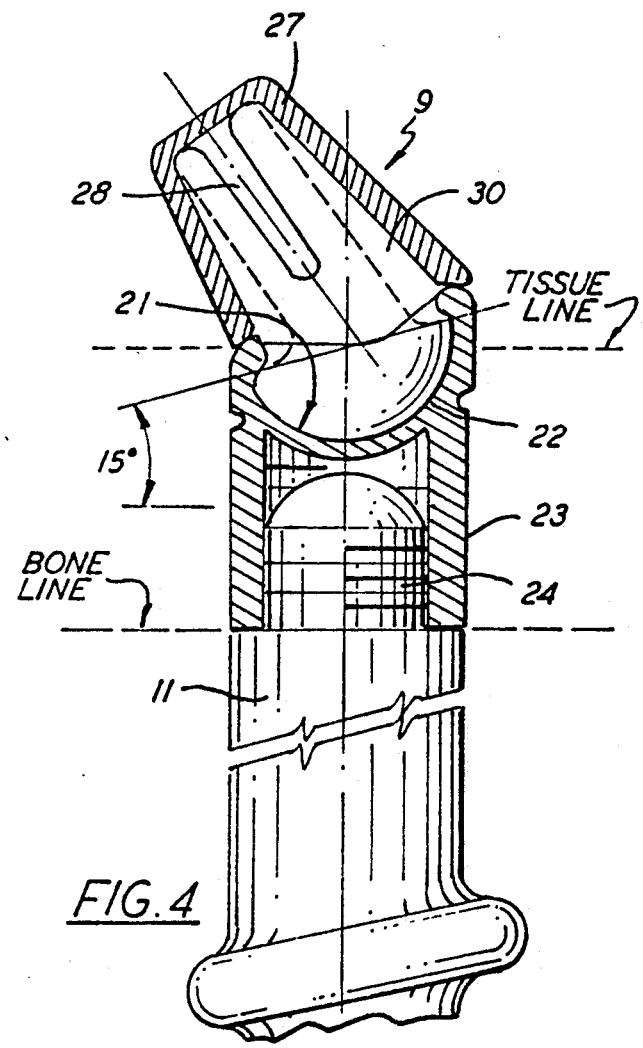

DENTAL IMPLANT

FIELD OF THE INVENTION

The invention pertains to dental implants, and more particularly to a dental implant that provides a controlled compressive force against an inner wall of a drilled and tapped hole in a jaw bone.

BACKGROUND OF THE INVENTION

Many different dental implant designs have been proposed and applied with varying degrees of success.

Submergible blade and screw-type implants have been shown to be the most popular form of dental implant in recent times. This type of implant works on the principle of "osseointegration", a term coined by Dr. Per-Ingvar Branemark of Sweden. Osseointegration is a process wherein bone grows towards the implant device. It is desired to have the bone grow through holes and vents in the implant, so that the implant becomes structurally integral with the jaw, thus stabilizing the implant.

One of the drawbacks to the above process (osteointegration) is that it requires many months to achieve the necessary bone growth, with no control or predictable results. Therefore, the doctor and patient cannot put the new teeth into immediate function, but rather must wait until nature decides to cooperate.

Another drawback of these devices is that they distribute uncontrolled biting forces in such a way that it is not always predictable whether enough support for masticatory forces will be provided by the implant to prevent failure.

More often than not poor bone physiology and heavy masticatory forces cause this implant to fail.

Screw-type implants have also been applied with varying success. This type of dental implant is designed to take an immediate hold within the jaw bone by the use of small sharp-pointed threads. The surface design of these threads contacts bone surface where possible, thus providing varying degrees of support due to the lack of physiologic integrity of bone following tooth extraction.

Unfortunately, however, the sharp-bladed threads often traumatize the bone, putting too much pressure on bone surfaces.

Therefore, this type of implant often cause necrosis of the bone tissue, and subsequent failure of the implant under masticatory loading, due to minimum structural support areas of the implant.

The present invention is based on the discovered osteocompression principle that proper bone physiology and masticatory support is achievable only by careful control of the osteocompressive forces exerted between the implant surface and the surrounding bone tissue of the jaw.

Controllable osteocompression is accomplished by increasing the surface area of implant support through novel geometric re-design of the conventional screws' over-all dimensions.

DISCUSSION OF RELATED ART

A screw-type implant having broad surfaced spiral passages is illustrated in U.S. Pat. No. 4,486,178; issued: Dec. 4, 1984. The sharp surfaced threads are not designed to provide the controlled compression forces to which the invention is directed.

A dental implant with rounded peripheral threads is shown in U.S. Pat. No. 3,590,485; issued: July 6, 1971.

This implant has a molded outer body having rounded peripheral threads. There is no teaching of whether it is used as a plug and forced into a prepared hole in the jaw bone.

In any event, this implant does not show or suggest drilling and/or tapping a hole prior to insertion of the implant, so as to provide a controlled overlap between implant threads and tapped wall threads, whereby a controlled compressive force can be obtained.

SUMMARY OF THE INVENTION

The invention relates to a dental implant having a shank comprising a rounded thread portion terminating in an end cap and an abutment disposed above the rounded thread portion for attaching a tooth prosthesis or bridge hardware to the shank.

A controlled compressive force is provided by the implant to the walls of a prepared hole in the jaw bone, which has been drilled and tapped. The controlled compressive force is achieved by the overlap between the rounded implant threads and the undercut tapped threads in the jaw bone wall.

It is an object of this invention to provide an improved screw-type implant.

It is another object of the invention to provide a dental implant having a controlled compressive force.

It is another object of this invention to increase the support surface area of an implant in the bone for the same osteotomy as a conventional implant.

BRIEF DESCRIPTION OF THE DRAWINGS

A complete understanding of the present invention may be obtained by reference to the accompanying drawings, when taken in conjunction with the detailed description thereof and in which:

FIG. 1 a front view of the dental implant of this invention;

FIG. 4 is a sectional view of a universal-type abutment for the dental implant of FIG. 1.

DESCRIPTION OF THE PREFERRED EMBODIMENT

Figures 2, 3:
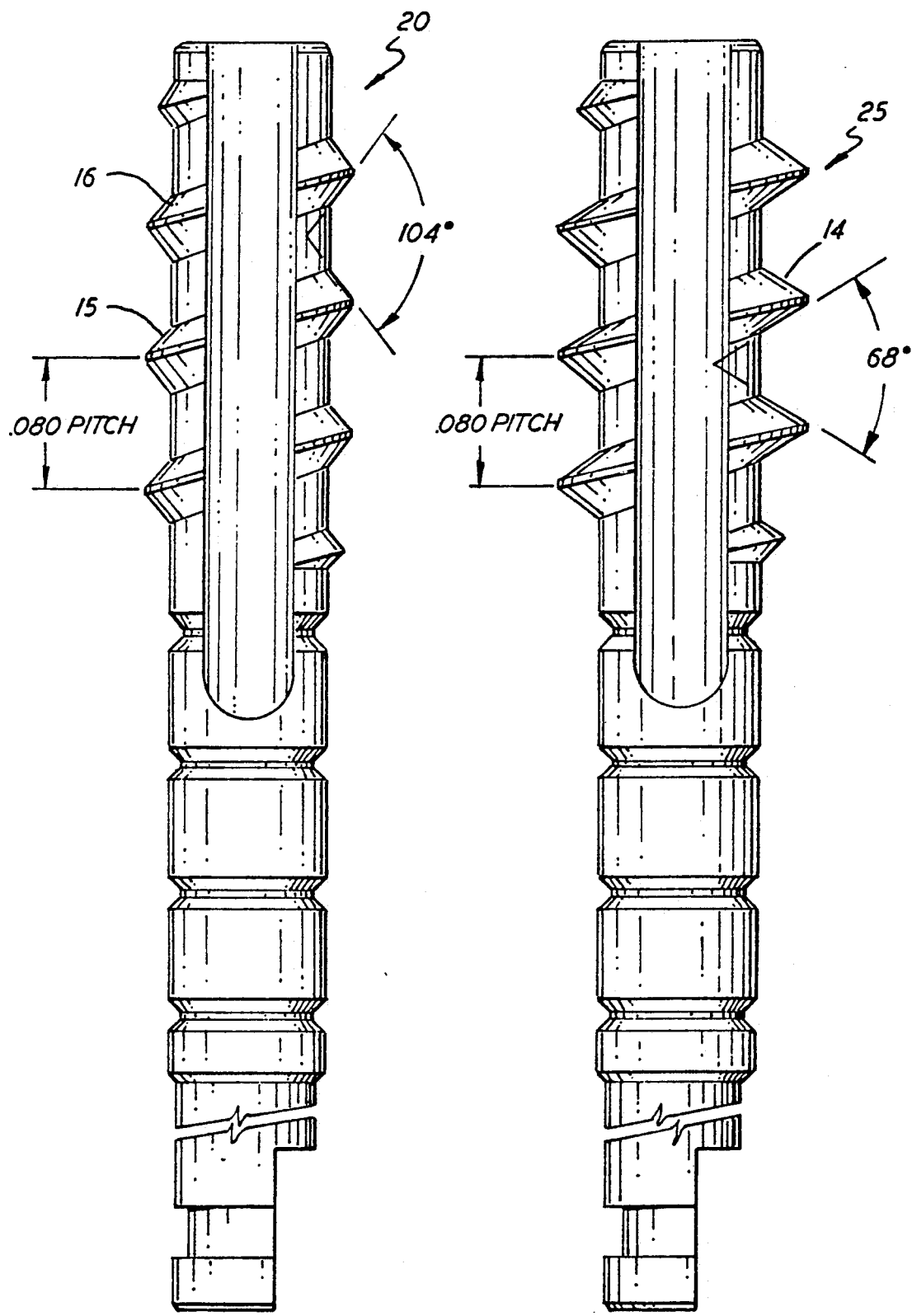
FIG. 2 is a partial view of the threads of a preliminary tap used in conjunction with a spade drill to prepare the drilled hole of a jaw bone for the screwed insertion of the implant of FIG. 1 into maxillary or mandibular bone of the jaw.
FIG. 3 is a partial view of the threads of a secondary tap for increasing the wall threads of the preliminary tap for preparing the bone of the jaw for the screwed insertion of the implant shown in FIG. 1.

Generally speaking, the invention features a screw-type implant that provides for controlled compressive forces against the wall of the jaw bone. The bone is prepared by a spade drill of a specific diameter, followed by a primary and secondary tap in order to form an atraumatic undercut thread. The rounded threads of the implant provide a controlled radial force against the undercut threads that is specifically engineered to be sufficient to support the masticatory loads on the implant and provide a laminated interface against the implant, such as natural teeth provide in the host bone.

Now referring to FIG. 1 the dental implant 10 of this invention is shown. The dental implant 10 has a shank 11 upon which a universal abutment 9 is schematically shown, and will be explained in more detailed hereinafter, with reference to FIG. 4. The universal abutment is used to attach a tooth prosthesis or bridge hardware to shank 11.

Below the shank 11 is a length of rounded screw threads 12 of a smooth, given radial surface 18. The rounded screw threads 12 terminate in a rounded cap 13 and have an approximate length of 13 mm excluding the cap.

All of the surfaces 18 and 13, are respectively smoothly rounded to provide radial forces at points of contact within the jaw bone.

The pitch span between curved threads is approximately 0.08 inch, and the major and minor diameter of the threads is 0.16 and 0.10 inches across, respectively.

The dental implant 10 is screwed into a prepared hole (not shown) in the jaw bone of a patient. A slow speed (between 1000 to 1500 rpm) spade drill (not shown) having an outside diameter of 0.10 inches is used for this purpose.

Next a single or a double tap is used to cut threads into the wall of the drilled hole.

FIGS. 2 and 3 illustrate a preliminary tap 20 and a secondary tap 25, respectively. The preliminary tap 20 is used at a slow speed (between 0–18 r.p.m.) in maxillary bone and features threads 16 with an engineered surface 15 of a given angle of 104° and outside diameter of 0.130 inches.

The given angle of 104° provides surface 15 with a cutting profile of proper undercut with respect to the rounded radial surface 18 of threads 12. This is more clearly shown in FIG. 1, where the difference in wall area between these two threads is shown as area 17.

When the implant 10 is to be used in mandibular bone tissue, the secondary tap 25 of FIG. 3 is used at a slow speed (between 0–18 r.p.m.) in conjunction with the first tap 20, to further reduce the undercut area between the thread surface 18 and tap thread surface 14 having an outside diameter of 0.160 inches.

Tap thread surface 14 of tap 25 has a profile provided by the 68° angle of pitch. The resultant differential area 19 between surface 14 and surface 18 is illustrated in FIG. 1.

When the threads 12 are screwed into the drilled and tapped hole, threads 12 being greater in profile than the threaded tapped surface will cause a compressive force of a calculated and controlled value to be exerted upon the jaw bone tissue. In this manner, the implant 10 will provide enough holding strength against masticatory loads, due to the increased design of surface area of implant support, but not too much force as to cause necrosis.

Referring to FIG. 4, the universal abutment 9 of FIG. 1 is depicted in more detail. The abutment 9 has a ball surface 21 that fits within a rounded ball socket 22. A threaded cap 23 screws onto the top 24 of shank 11.

The ball surface 21 is part of a mounting post 30 upon which a tooth prosthesis 27 is attachable. A wire band (not shown) of a bridge apparatus can also be fitted to post 30 via slot 28, as disclosed in U.S. Pat. Nos. 3,866,321; 3,881,251; and 3,548,499.

The universal abutment 9 can swing, via ball surfaces 21 and 22, in any direction, such that the tooth prosthesis can be attached at almost any angle. This allows the implant 10 to be fitted in the jaw bone at the most advantageous position without affecting the angle of the prosthesis with respect to the gum line.

Having thus described the invention what is desired to be protected by Letters Patent is presented by the appended claims.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A dental implant and tap combination for threaded insertion of said dental implant into a drilled and tapped bore hole having tapped wall threads created by a first tap for tapping into maxillary bone and a second tap for tapping into mandibular bone, said drilled and tapped bore hole providing a bore hole wall of undercut threads for the subsequent threading of said dental implant, said dental implant having a thread length of rounded threads, said rounded threads of said dental implant radially extending beyond an outer diameter of threads of said first or second tap causing compression against the wall of said undercut threads and said bore hole, whereby a controlled compressive force is provided by the threaded dental implant against said bore hole wall in said jaw bone for providing sufficient holding strength to withstand masticatory loads, but insufficient compression for causing necrosis.

2. The dental implant and tap combination of claim 1, wherein tapping into mandibular bone requires less compressive force to hold said dental implant than does single tapped maxillary bone, wherein said second tap provides a bore hole wall with secondary undercut threads of a greater depth of cut, whereby a lesser compressive force is provided by the subsequently threaded dental implant against the bore hole wall of said maxillary bone.

3. The dental implant and tap combination of claim 2, further comprising a resorbable hydroxylapatite coating disposed upon said dental implant, wherein said dental implant is prepared by grouting with an application of resorbable hydroxylapatite prior to threading said dental implant into said bore hole.

4. The dental implant and tap combination of claim 2, wherein said second tap has a pitch angle between threads of less than 75°.

5. The dental implant and tap combination of claim 4, wherein said pitch angle is approximately 68°.

6. The dental implant and tap combination of claim 1, further comprising a resorbable hydroxylapatite coating disposed upon said dental implant, wherein said dental implant is prepared by grouting with an application of resorbable hydroxylapatite prior to threading said dental implant into said bore hole.

7. The dental implant and tap combination of claim 1, further comprising a universal abutment disposed adjacent said length of rounded threads for attachment of a tooth prosthesis or bridge hardware to said dental implant at a given angle with a range of attachment angles.

8. The dental implant and tap combination of claim 1, wherein said first tap threads have a pitch angle between threads of greater than 90°.

9. The dental implant and tap combination of claim 8, wherein said pitch angle of the threads of said first tap is approximately 104°.

10. The dental implant and tap combination of claim 1, wherein said thread length of said rounded threads terminates in a rounded cap.

11. The dental implant and tap combination of claim 1, wherein said thread length is approximately 13 mm.

12. The dental implant and tap combination of claim 1, wherein a pitch span between rounded threads is approximately 0.08 inch.

13. The dental implant and tap combination of claim 1, wherein a major diameter of said rounded threads is approximately 0.16 inches across.

14. The dental implant and tap combination of claim 1, wherein a minor diameter of said rounded threads is approximately 0.10 inches across.

15. A method of utilizing a dental implant for providing a controlled compressive force to a threaded wall in a bore hole that is drilled and tapped into a jaw bone, said threaded wall having undercut threads and said dental implant having rounded threads that radially extend a given distance beyond said undercut threads to provide an overlap between the threads of said bore hole and the threads of said implant, whereby a controlled compressive force is created between said dental implant and said thread wall of the bore hole in order to immediately bind said dental implant to said jaw bone.

16. The dental implant method of claim 15, wherein said drilled and tapped threaded wall is tapped into maxillary bone by a preliminary tap.

17. The dental implant method of claim 15, wherein said drilled and tapped threaded wall is tapped into mandibular bone by both a preliminary tap followed by a secondary tap.

18. The dental implant method of claim 15, further comprising the step of applying ceramic hydroxylapatite coating to a surface of said rounded threads.

19. The dental implant method of claim 15, wherein said rounded threads terminate in a rounded cap.

20. The dental implant method of claim 15, wherein a universal abutment is disposed above said rounded threads, and said method further comprises the step of attaching a tooth prosthesis or bridge hardware to said dental implant at a given angle within a range of attachment angles.

* * * * *